United States Patent
Xiang (10) Patent No.: US 10,835,690 B2
(45) Date of Patent: Nov. 17, 2020

(54) PUNCTURE DEPTH CONTROLLING AND NEEDLE HIDING DEVICE AND USAGE METHOD THEREOF

(71) Applicant: Wen Xiang, Jiangsu (CN)

(72) Inventor: Wen Xiang, Jiangsu (CN)

( * ) Notice: Subject to any disclaimer, the term of this patent is extended or adjusted under 35 U.S.C. 154(b) by 113 days.

(21) Appl. No.: 16/003,101

(22) Filed: Jun. 7, 2018

(65) Prior Publication Data

US 2018/0289902 A1   Oct. 11, 2018

Related U.S. Application Data (63) Continuation of application No. PCT/CN2015/093470, filed on Oct. 30, 2015.

(51) Int. Cl.
  *A61M 5/46* (2006.01)
  *A61M 5/32* (2006.01)

(52) U.S. Cl.
  CPC .............. *A61M 5/46* (2013.01); *A61M 5/326* (2013.01); *A61M 5/3271* (2013.01); *A61M 2005/3267* (2013.01); *A61M 2205/0216* (2013.01); *A61M 2205/583* (2013.01); *A61M 2205/59* (2013.01); *A61M 2209/00* (2013.01)

(58) Field of Classification Search
  CPC ...... A61M 5/46; A61M 5/326; A61M 5/3271; A61M 5/3272; A61M 5/3269; A61M 5/34; A61M 5/346; A61M 5/345; A61M 5/344; A61M 2005/3267; A61M 2005/3268; A61M 2205/59; A61M 2205/583; A61M 2205/0216; A61M 2209/00
  See application file for complete search history.

(56) References Cited

U.S. PATENT DOCUMENTS

| | | | | |
|---|---|---|---|---|
| 5,250,026 A | * | 10/1993 | Ehrlich | A61M 37/0069 604/117 |
| 2003/0050655 A1 | * | 3/2003 | Roe | A61B 5/150259 606/182 |

(Continued)

FOREIGN PATENT DOCUMENTS

| | | |
|---|---|---|
| CN | 203154486 U | 8/2013 |
| WO | 2013121307 A1 | 8/2013 |
| WO | WO-2013121307 A1 * | 8/2013 .............. A61M 5/46 |

OTHER PUBLICATIONS

International Search Report of PCT Patent Application No. PCT/CN2015/093470 dated Jul. 27, 2016.

*Primary Examiner* — Bhisma Mehta
*Assistant Examiner* — Hong-Van N Trinh (57) ABSTRACT

Disclosed is a puncture depth controlling and needle hiding device and a usage method thereof. The puncture depth controlling and needle hiding device comprises a housing and an inner sleeve. The inner sleeve is positioned in the housing and is rotatable. Correspondingly matched limiting structures are provided on an inner wall of the housing and an outer wall of the inner sleeve. A spring is provided between the housing and the inner sleeve to push the proximal ends of the housing and the inner sleeve to be separated and keep the inner sleeve at an initial axial position with respect to the housing. By means of the invention, the medicinal liquid injection operation is simplified, and the need insertion depth is accurate. A needle hiding structure reduces the risk of accidental stab.

8 Claims, 7 Drawing Sheets

(56) References Cited

U.S. PATENT DOCUMENTS

| | | | | |
|---|---|---|---|---|
| 2010/0094216 A1* | 4/2010 | Yue | ........................ | A61M 5/46 |
| | | | | 604/117 |
| 2011/0028909 A1* | 2/2011 | Lum | .................... | A61M 5/344 |
| | | | | 604/192 |
| 2014/0207167 A1* | 7/2014 | Schraga | ............... | A61B 5/1411 |
| | | | | 606/182 |

* cited by examiner

PUNCTURE DEPTH CONTROLLING AND NEEDLE HIDING DEVICE AND USAGE METHOD THEREOF

CROSS REFERENCE TO RELATED APPLICATIONS

The present application is a Continuation Application of PCT Application No. PCT/CN2015/093470 filed on Oct. 30, 2015, the contents of which are hereby incorporated by reference.

TECHNICAL FIELD

The present invention relates to the field of medical instruments, and in particular to a puncture depth controlling and needle hiding device and a usage method thereof, applicable to self-administration medicine injection, for example, insulin injection.

RELATED ART

Injection administration is a method commonly adopted in modern medical treatment, and is generally used in the case that drugs are not recommended for oral administration, and drug effects should be quickly achieved according to medical necessity, wherein multiple injection methods such as subcutaneous injection and intramuscular injection are involved. Subcutaneous injection and intramuscular injection are made in specific parts, and the needle insertion depths have different requirements, respectively.

Take insulin injection therapy for controlling blood glucose for example, insulin injection is a type of subcutaneous injection, the preferred injection parts comprise restricted parts of the abdomen, lateral thigh, upper arm, and hip. Only when insulin is injected in the subcutaneous layer of fat, it is beneficial to slow absorption of insulin into the blood to achieve a better therapeutic effect, and the optimal preferred solution is: vertically inserting and withdrawing the syringe needle quickly, the needle insertion depth is about 4 mm. If the syringe needle is inserted shallow, insulin cannot be injected to the subcutaneous layer of fat, and the risk of failing to achieve the therapeutic effect is high. If the syringe needle is inserted deeply to the muscle, since there are many blood vessels in muscle, insulin would be quickly absorbed, or may cause hypoglycemia, and the stated insulin therapeutic effect cannot be achieved. However, the current commercially available syringe needles matching the injectors are different in length, including multiple specifications of syringe needles with the length of 4-13 mm; these syringe needles do not provide injection to the subcutaneous space by the optimal penetration depth of 4 mm. Therefore, since the injection skill requirement is high, the operator should be trained, and generally, the injector is handheld by a doctor or nurse to operate by cooperation of both hands: one hand kneads the skin, and the other hand holds the insulin injector, quickly pierces the syringe needle to the injection part at an angle of 45°, and then pushes the medicinal liquid.

At present, frequent injection is required due to these diseases. Self-administration injection requirements for non-professional medical personnel at non-medical sites are more and more common. The risks of injected dose error, deep insertion, erroneous insertion, needle breakage and so on are high. Moreover, since the syringe needle is exposed, the patient can intuitively and clearly see the syringe needle and thus feels anxious and fear, and as a result, it is inconvenient to use.

SUMMARY

The technical problem to be solved by the present invention is to provide a puncture depth controlling and needle hiding device and a usage method thereof. The device matches multiple types of commercially available injectors and syringe needles of various lengths matching the injectors, vertically inserting and withdrawing the needle quickly can be achieved by a single hand for injection under an optimal injection depth, and the device is applicable to self-administration optimization injection of different populations in different parts. Moreover, the exposed needle is hidden, relieving fear of the self-administration operator, and it is convenient to use.

The present invention is achieved through the following technical solution:

a puncture depth controlling and needle hiding device, comprising a housing and an inner sleeve capable of accommodating and joining an injector; the inner sleeve is positioned in the housing and can axially move and circumferentially rotate; several correspondingly matched axial stroke limiting structures are provided on an inner wall of the housing and an outer wall of the inner sleeve, respectively; the housing and the inner sleeve are each provided with an opening on their respective distal end and a through hole on their respective proximal end, a spring is provided between the housing and the inner sleeve, and both ends of the spring are respectively abutted against the inner wall of the proximal end of the housing and the outer wall of the proximal end of the inner sleeve to push the proximal ends of the housing and the inner sleeve to be separated and keep the inner sleeve at an initial axial position with respect to the housing; a length marking element and a directional sign element which correspond to a syringe needle of the injector are provided on the peripheral surfaces of the housing and the inner sleeve, respectively.

A further improved solution of the present invention is that: the axial stroke limiting structures provided on the outer wall of the inner sleeve are flanges stepwise distributed in the circumferential direction, and corresponding axial stroke limiting structures provided on the inner wall of the housing are ribs extending in the axial direction. The tops of the ribs are abutted against the flanges of different heights to define the axial downstream depth of the inner sleeve, so that the syringe needles of different lengths protrude out of the through hole on the proximal end of the housing by equal lengths to achieve the optimal preferred setting of the injection depth.

Another improved solution of the present invention is that: the axial stroke limiting structures provided on the outer wall of the inner sleeve are elastic ribs provided in the axial direction, and corresponding axial stroke limiting structures provided on the inner wall of the housing are step-like grooves extending in the axial direction and distributed on a circumferential wall at intervals.

A further improved solution of the present invention is that: a shell cover is sleeved at the periphery of the inner sleeve, the inner diameter of the shell cover is greater than the outer diameter of an inner sleeve body and is smaller than the outer diameter of an annular part enclosed by the axial stroke limiting structures at the middle of the inner sleeve, and the shell cover is fixedly assembled with the housing to position the inner sleeve in the housing. The shell cover enables the sleeve and the housing to be integrally combined, and is suitable for operation.

A further improved solution of the present invention is that: several axial guide slots or guide rails are provided on the inner wall of the housing; at least one radially deformed elastic structure is provided at the middle of the inner sleeve; the elastic structure is an elastic member whose three sides or two sides are separated from the inner sleeve body; the elastic member is provided with bumps or grooves; the bumps are snap-fit to the guide slots, or the guide rails are snap-fit to the grooves to guide the inner sleeve to axially move; the inner sleeve circumferentially rotates, and the bumps turn aside a convex surface on which the guide slots are formed under the action of the elastic member. The bumps match the guide slots to guide the inner sleeve to axially move relative to the housing, and moreover, due to certain radial deformation, the elastic structure can also turn aside the convex surface on which the guide slots are formed when the inner sleeve circumferentially rotates, and the structure is rational.

A further improved solution of the present invention is that: the distal end of the inner sleeve is sleeved with an outer sleeve, and an inner wall of the outer sleeve is provided with an inner surface connected to an outer wall of the injector. Since the specifications of the outer diameters of the injectors that can be accommodated and joined in the inner sleeve are different, the inner sleeve of the same diameter can only match one injector. The inner sleeve has a complex structure and high manufacturing costs. In order to improve the universality of the inner sleeve, an outer sleeve matching different injectors is sleeved on the distal end of the inner sleeve, without changing the inner diameter of the inner sleeve.

A further improved solution of the present invention is that: an elastic cylinder is sleeved in the inner sleeve or the outer sleeve, the diameter of the lower section of the elastic cylinder is gradually decreased, a circumferential wall of the lower section is provided with at least one axial notch, the elastic cylinder radially deforms, and an inner wall of the elastic cylinder is provided with an inner surface connected to an inner wall of the injector. The inner diameter of the inner sleeve or the outer sleeve is still limited to some extent. An elastic cylinder is added in the inner sleeve or the outer sleeve so that the device of the same specification is suitable for injectors having a wider range of outer diameter specifications.

A further improved solution of the present invention is that: the periphery of the through hole on the proximal end of the housing is provided with an annular boss, and an end face of the boss is concave. The end face of the boss first contacts the concave target part during injection so that needle insertion and medicinal liquid pushing are more stable.

A further improved solution of the present invention is that: the boss is made of elastomer materials. A person feels comfortable when the boss contacts the target part.

A further improved solution of the present invention is that: the outer wall of the inner sleeve is provided with convex or concave scale lines. Rotating the housing makes the directional sign element on the inner sleeve correspond to the length marking element of the syringe needle of the injector on the housing, the inner sleeve is pressed to observe whether the insertion depth scale lines of the inner sleeve are consistent so as to inspect whether the device is qualified, and observe and calculate the distance of the moving stroke.

A usage method of a puncture depth controlling and needle hiding device, comprising:

step (1), selecting the puncture depth controlling and needle hiding device and an injector, and rotating a housing of the device according to the length of a syringe needle matching the injector to enable a directional sign element to correspond to a length marking element of the syringe needle of the injector;

step (2), putting and joining the prepared injector into an inner sleeve, keeping the device in the front of the injector, and hiding the syringe needle in the front of the injector in the housing;

step (3), holding the injector to vertically hit against a selected target part, making a proximal end of the housing of the device first contact and stay on a surface of the target part, continuing pushing the inner sleeve to axially move from an initial axial position to the proximal end by the injector, and limiting the syringe needle to protrude out of a through hole on the proximal end of the housing to be inserted and kept at the target part;

step (4), further operating the injector to finish medicinal liquid pushing; and step (5), vertically pulling out the injector together with the syringe needle, returning the inner sleeve to the initial axial position, and automatically hiding the syringe needle in the front of the injector in the housing.

The effects of the present invention are as follows:

The present invention reduces the technical difficulty of medicinal liquid injection operation and improves the operation efficiency, can match multiple types of commercially available injectors and syringe needles of various lengths matching the injectors, vertically inserting and withdrawing the needle quickly can be achieved by a single hand for subcutaneous injection under an optimal injection depth to the utmost extent, so as to ensure the effect of medicinal liquid injection. Moreover, the exposed needle is hidden, reducing the risk of accidental stab and needle breakage, relieving anxiety and fear of an operator and meeting the demands for self-administration optimization injection of different populations.

DETAILED DESCRIPTION

Embodiment 1

As shown in FIGS. 1-5, the present invention comprises a housing 1 and an inner sleeve 3 capable of accommodating and joining an injector; the inner sleeve 3 is positioned in the housing 1 and can axially move and circumferentially rotate; several correspondingly matched axial stroke limiting structures are provided on an inner wall of the housing 1 and an outer wall of the inner sleeve 3, respectively; the axial stroke limiting structures provided on the outer wall of the inner sleeve 3 are flanges 32 stepwise distributed in the circumferential direction, and corresponding axial stroke limiting structures provided on the inner wall of the housing 1 are ribs 12 extending in the axial direction; the housing and the inner sleeve are each provided with an opening on their respective distal end and a through hole on their respective proximal end, a spring 2 is provided between the housing 1 and the inner sleeve 3, and both ends of the spring 2 are respectively abutted against the inner wall of the proximal end of the housing and the outer wall of the proximal end of the inner sleeve to push the proximal ends of the housing 1 and the inner sleeve 3 to be separated and keep the inner sleeve 3 at an initial axial position with respect to the housing 1; a length marking element 11 and a directional sign element 31 which correspond to a syringe needle of the injector are provided on the peripheral surfaces of the housing 1 and the inner sleeve 3, respectively.

The inner sleeve 3 is made of a material having a good self-lubricating property, such as POM, PA, PEEK, and PTFE resins. The surface of the spring 2 provided between the housing 1 and the inner sleeve 3 is at least partially coated with a damping material.

A shell cover 4 is sleeved at the periphery of the inner sleeve 3, the inner diameter of the shell cover 4 is greater than the outer diameter of an inner sleeve body and is smaller than the outer diameter of an annular part enclosed by the axial stroke limiting structures at the middle of the inner sleeve, and the shell cover 4 is fixedly assembled with the housing 1 to position the inner sleeve 3 in the housing 1.

Several axial guide slots 13 are provided on the inner wall of the housing 1; at least one radially deformed elastic structure is provided at the middle of the inner sleeve 3; the elastic structure is an elastic member 33 whose three sides or two sides are separated from the inner sleeve body; the elastic member 33 is provided with bumps 34; the bumps 34 are engaged with the guide slots 13 to guide the inner sleeve 3 to axially move; the inner sleeve 3 circumferentially rotates, and the bumps 34 turn aside a convex surface 14 on which the guide slots are formed under the action of the elastic member 33.

The distal end of the inner sleeve 3 is sleeved with an outer sleeve 5, and an inner wall of the outer sleeve 5 is provided with an inner surface connected to an outer wall of the injector. An elastic cylinder 6 is sleeved in the outer sleeve 5, the diameter of the lower second of the elastic cylinder 6 is gradually decreased, a circumferential wall of the lower second is provided with at least one axial notch 61, the elastic cylinder 6 radially deforms, and an inner wall of the elastic cylinder 6 is provided with an inner surface connected to an inner wall of the injector.

The periphery of the through hole on the proximal end of the housing 1 is provided with an annular boss 15, and end face 16 of the boss is concave. The annular boss 15 is made of elastomer materials, which may be silica gel, and may also be thermoplastic elastomers and the like.

The outer wall of the inner sleeve 3 is provided with convex scale lines 35.

A usage method of a puncture depth controlling and needle hiding device, comprising:

step (1), selecting the puncture depth controlling and needle hiding device according to any one of claims 1-9 and an injector, and rotating a housing of the device according to the length of a syringe needle matching the injector to enable a directional sign element on the inner sleeve to correspond to a length marking element of the syringe needle of the injector on the housing;

step (2), putting and joining the prepared injector into an inner sleeve, keeping the device in the front of the injector, and hiding the syringe needle in the front of the injector in the housing;

step (3), holding the injector to vertically hit against a selected target part, making a proximal end of the housing of the device first contact and stay on a surface of the target part, continuing pushing the inner sleeve to axially move from an initial axial position to the proximal end by the injector, and limiting the syringe needle to protrude out of a through hole on the proximal end of the housing to be inserted and kept at the target part;

step (4), further operating the injector to finish medicinal liquid pushing; and step (5), vertically pulling out the injector together with the syringe needle, returning the inner sleeve to the initial axial position, and automatically hiding the syringe needle in the front of the injector in the housing.

Embodiment 2

Figure 1:
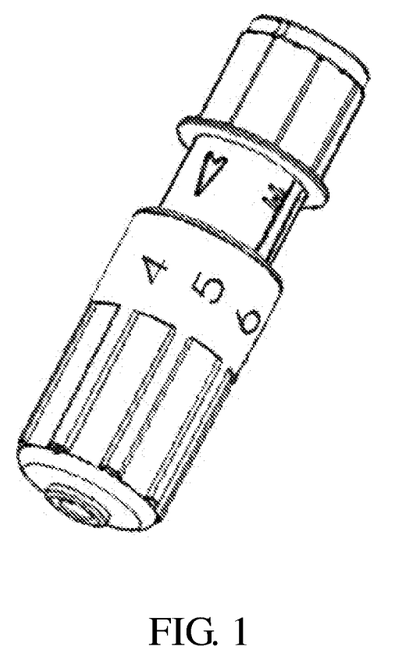
FIG. 1 is a stereogram of the present invention.
Figure 2:
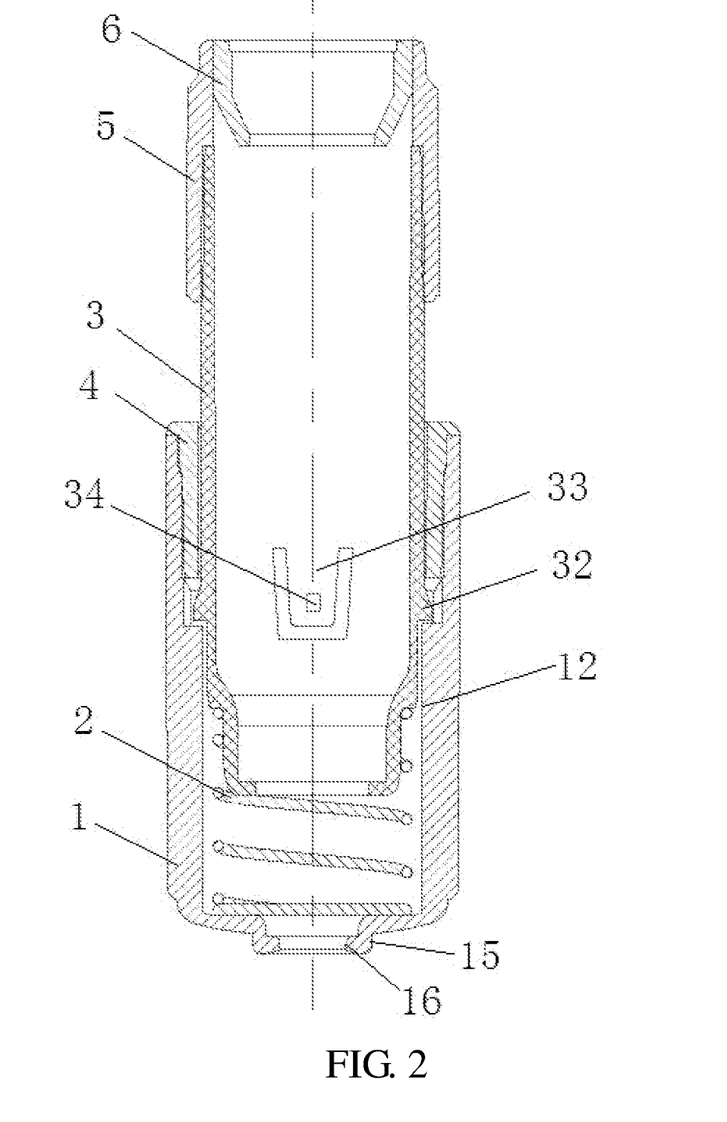
FIG. 2 is a section view of the present invention.
Figure 3:
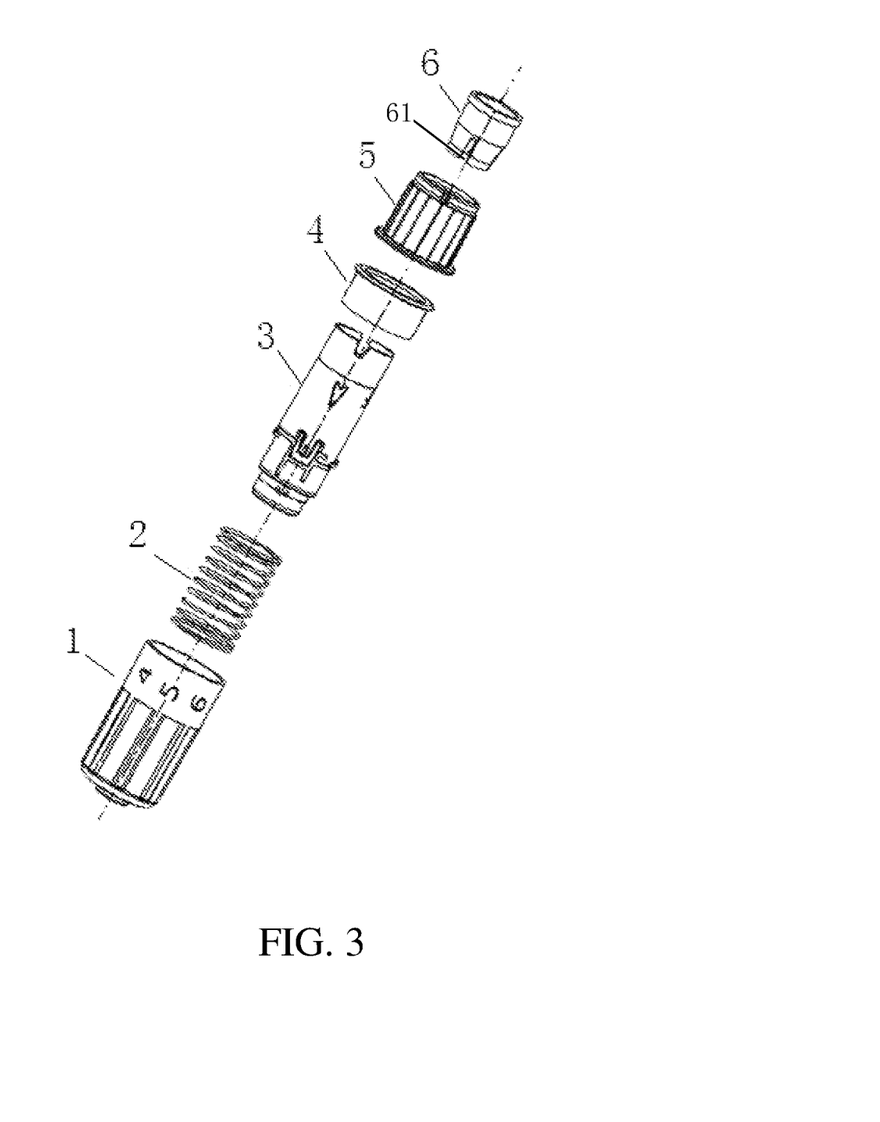
FIG. 3 is a stereoscopic exploded view of the present invention.
Figure 4:
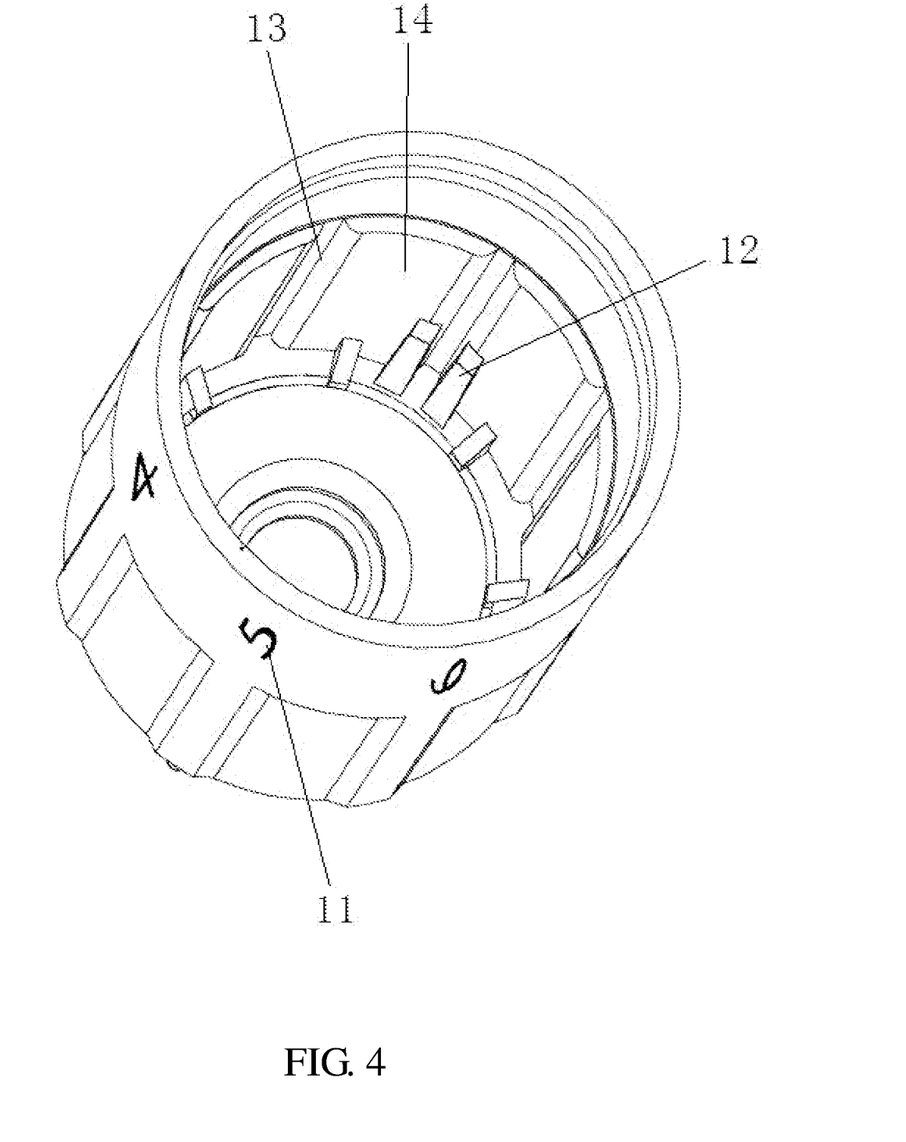
FIG. 4 is a stereogram of a housing in Embodiment 1 of the present invention.
Figure 5:
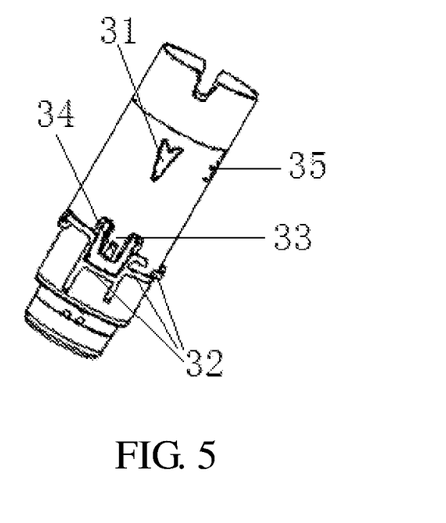
FIG. 5 is a stereogram of an inner sleeve in Embodiment 1 of the present invention.
Figure 6:
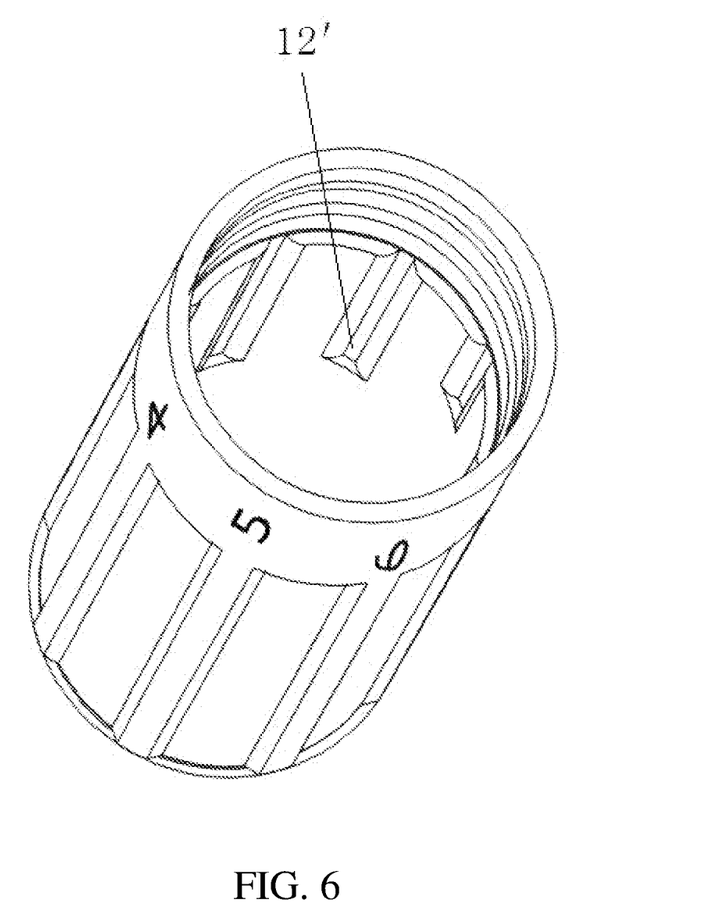
FIG. 6 is a stereogram of the housing in Embodiment 2 of the present invention.
Figure 7:
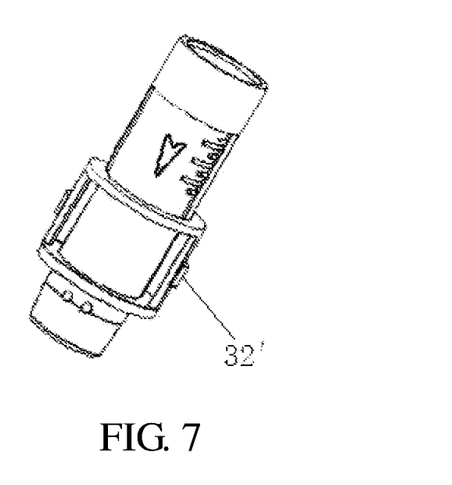
FIG. 7 is a stereogram of the inner sleeve in Embodiment 2 of the present invention.

As shown in FIGS. 6 and 7, the axial stroke limiting structures provided on the outer wall of the inner sleeve 3 are elastic ribs 32' provided in the axial direction, and corresponding axial stroke limiting structures provided on the inner wall of the housing are step-like grooves 12' extending in the axial direction distributed on a circumferential wall at intervals. The remaining features are the same as those of Embodiment 1.

It should be recognized that the structure introduced and displayed therein can be substituted with an equivalent structure, and embodiments of the present invention are not structures merely used for implementing the present invention. Although preferred embodiments of the present invention are displayed and introduced, it is obvious to those skilled in the art that these embodiments are proposed in the mode of examples. Those skilled in the art can make various variations, changes and substitutions without departing from the spirit of the present invention. For example, in use, the directional sign element 31 and the length marking element 11 are correspondingly combined for different directions, the length of the syringe needle protruding out of the through hole on the proximal end of the housing is purposively controlled to meet the injection requirements of populations of different skin thicknesses. Therefore, the scope of protection of the present invention should be based on the scope of protection defined in the claims.

What is claimed is:

1. A puncture depth controlling and needle hiding device, comprising a housing (1) and an inner sleeve (3) capable of accommodating and joining an injector, wherein the inner sleeve (3) is positioned in the housing (1) and can axially move and circumferentially rotate; several correspondingly matched axial stroke limiting structures are provided on an inner wall of the housing (1) and an outer wall of the inner sleeve (3), respectively; the housing and the inner sleeve are each provided with an opening on their respective distal end and a through hole on their respective proximal end, a spring (2) is provided between the housing (1) and the inner sleeve (3), and both ends of the spring (2) are respectively abutted against the inner wall of the proximal end of the housing and the outer wall of the proximal end of the inner sleeve to push the proximal ends of the housing (1) and the inner sleeve (3) to be separated and keep the inner sleeve (3) at an initial axial position with respect to the housing (1); a length marking element (11) and a directional sign element (31) which correspond to a syringe needle of the injector are provided on peripheral surfaces of the housing (1) and the inner sleeve (3), respectively;

wherein a shell cover (4) is sleeved at a periphery of an inner sleeve (3), an inner diameter of the shell cover (4)

is greater than an outer diameter of an inner sleeve body and is smaller than an outer diameter of an annular part enclosed by the correspondingly matched axial stroke limiting structures at a middle of the inner sleeve, and the shell cover (4) is fixedly assembled with the housing (1) to position the inner sleeve (3) in the housing (1).

2. The puncture depth controlling and needle hiding device according to claim 1, wherein the correspondingly matched axial stroke limiting structures provided on the outer wall of the inner sleeve (3) are flanges (32) stepwise distributed in a circumferential direction, and the correspondingly matched axial stroke limiting structures provided on the inner wall of the housing (1) are ribs (12) extending in an axial direction; or the correspondingly matched axial stroke limiting structures provided on the outer wall of the inner sleeve (3) are elastic ribs (32') provided in the axial direction, and the correspondingly matched axial stroke limiting structures provided on the inner wall of the housing are step-like grooves (12') extending in the axial direction and distributed on a circumferential wall at intervals.

3. The puncture depth controlling and needle hiding device according to claim 1, wherein several axial guide slots (13) or guide rails are provided on the inner wall of the housing (1); at least one radially deformed elastic structure is provided at the middle of the inner sleeve (3); the at least one radially deformed elastic structure is an elastic member (33) whose three sides or two sides are separated from the inner sleeve body; the elastic member (33) is provided with bumps (34) or grooves; the bumps (34) are engaged with the several axial guide slots (13), or the guide rails are engaged with the grooves to guide the inner sleeve (3) to axially move; the inner sleeve (3) circumferentially rotates, and the bumps (34) turn aside a convex surface (14) on which the several axial guide slots (13) are formed under an action of the elastic member (33).

4. The puncture depth controlling and needle hiding device according to claim 1, wherein the distal end of the inner sleeve (3) is sleeved with an outer sleeve (5), and an inner wall of the outer sleeve (5) is provided with an inner surface connected to an outer wall of the injector.

5. The puncture depth controlling and needle hiding device according to claim 1, wherein a periphery of the through hole on the proximal end of the housing (1) is provided with an annular boss (15), and an end face (16) of the annular boss is concave.

6. The puncture depth controlling and needle hiding device according to claim 5, wherein the annular boss (15) is made of elastomer materials.

7. The puncture depth controlling and needle hiding device according to claim 1, wherein the outer wall of the inner sleeve (3) is provided with convex or concave scale lines (35).

8. A puncture depth controlling and needle hiding device, comprising a housing (1) and an inner sleeve (3) capable of accommodating and joining an injector, wherein the inner sleeve (3) is positioned in the housing (1) and can axially move and circumferentially rotate; several correspondingly matched axial stroke limiting structures are provided on an inner wall of the housing (1) and an outer wall of the inner sleeve (3), respectively; the housing and the inner sleeve are each provided with an opening on their respective distal end and a through hole on their respective proximal end, a spring (2) is provided between the housing (1) and the inner sleeve (3), and both ends of the spring (2) are respectively abutted against the inner wall of the proximal end of the housing and the outer wall of the proximal end of the inner sleeve to push the proximal ends of the housing (1) and the inner sleeve (3) to be separated and keep the inner sleeve (3) at an initial axial position with respect to the housing (1); a length marking element (11) and a directional sign element (31) which correspond to a syringe needle of the injector are provided on peripheral surfaces of the housing (1) and the inner sleeve (3), respectively; wherein the distal end of the inner sleeve (3) is sleeved with an outer sleeve (5), and an inner wall of the outer sleeve (5) is provided with an inner surface connected to an outer wall of the injector, wherein an elastic cylinder (6) is sleeved in the inner sleeve (3) or the outer sleeve (5), a diameter of a lower section of the elastic cylinder (6) is gradually decreased, a circumferential wall of the lower section is provided with at least one axial notch (61), the elastic cylinder (6) radially deforms, and an inner wall of the elastic cylinder (6) is provided with an inner surface connected to an inner wall of the injector.

* * * * *